(12) United States Patent
Carpentier

(10) Patent No.: US 8,753,867 B2
(45) Date of Patent: Jun. 17, 2014

(54) METHOD OF EVALUATING THE BIODEGRADATION OF HYDROCARBONS TRAPPED IN A BASIN

(75) Inventor: Bernard Carpentier, Labbeville (FR)

(73) Assignee: Institut Francais du Petrole, Rueil Malmaison (FR)

( * ) Notice: Subject to any disclaimer, the term of this patent is extended or adjusted under 35 U.S.C. 154(b) by 1919 days.

(21) Appl. No.: 11/478,616

(22) Filed: Jul. 3, 2006

(65) Prior Publication Data
US 2007/0007203 A1   Jan. 11, 2007

(30) Foreign Application Priority Data
Jul. 8, 2005   (FR) ...................................... 05 07417

(51) Int. Cl.
| | | |
|---|---|---|
| *C10G 99/00* | (2006.01) | |
| *C02F 3/34* | (2006.01) | |
| *A62D 3/00* | (2006.01) | |
| *A62D 3/02* | (2007.01) | |
| *B09C 1/10* | (2006.01) | |
| *C10G 32/00* | (2006.01) | |
| *C02F 3/02* | (2006.01) | |
| *C02F 3/04* | (2006.01) | |

(52) U.S. Cl.
USPC .......... 435/281; 435/29; 435/262; 435/262.5; 210/610

(58) Field of Classification Search
USPC .................. 435/29, 262, 262.5, 281; 210/610
See application file for complete search history.

(56) References Cited

U.S. PATENT DOCUMENTS

2005/0015228 A1   1/2005   Carpentier et al.

OTHER PUBLICATIONS

Lu et al. 1999. Natural Attenuation of BTEX Compounds: Model Development and Field-Scale Application, Ground Water, Sep.-Oct., vol. 37, No. 5, pp. 707-717.*
Head et al. "Biological activity in the deep subsurface and the origin of heavy oil", Nature, vol. 426, No. 20, 2003, pp. 344-352.
Z Allan et al.: "How to predict biodegration risk and reservoir fluid quality" Worldoil. Com, vol. 223, No. 4, 2002, pp. 1-11.
Larter et al.: "Biodegradation rates assessed geologically in a heavy oil field, implications for the deep, slow (Largo) biosphere Phenix Goldschimdt" Heavy Oilfield Biosphere, 2000, pp. 1-4.
Carpentier: "New concepts for biodegradation evaluation in oil fields, a combined geological and numerical approach" Annual Meeting Expanded Abstracts-American Association of Petroleum Geologists, Mar. 10, 2002, p. 27.

* cited by examiner

*Primary Examiner* — Jon P Weber
*Assistant Examiner* — Kailash C Srivastava
(74) *Attorney, Agent, or Firm* — Antonelli, Terry, Stout & Krause, LLP.

(57) ABSTRACT

Method of evaluating the biodegradation, through the action of a bacterial population, of hydrocarbons trapped in a geologic structure.

The mass of hydrocarbons present in said structure is determined without taking account of the biodegradation, from data relative to the physical and geometrical characteristics of the structure studied. Then the mass of hydrocarbons consumed by biodegradation is calculated after evaluating the number of bacteria, their hydrocarbon consumption and the structure filling time. The mass percentage of oil disappeared through the bacterial action is deduced from these two masses.

Application: determination of the composition of oils in a reservoir and notably location of heavy oils. The method can notably be applied to the evaluation of the economic risk linked with the presence of biodegraded petroleum reservoirs.

15 Claims, 3 Drawing Sheets

METHOD OF EVALUATING THE BIODEGRADATION OF HYDROCARBONS TRAPPED IN A BASIN

FIELD OF THE INVENTION

The present invention relates to a method of evaluating the biodegradation, linked with the action of a bacterial population, of hydrocarbons trapped in a geologic structure such as a petroleum reservoir.

The method according to the invention provides an evaluation tool that is notably very useful to geologists anxious to direct investigations outside risk zones.

One of the problems commonly encountered when defining the interest of an oil play, i.e. a non-drilled hydrocarbon trap, located at a relatively low temperature (usually less than 80° C.), is the evaluation of the risk of "biodegradation". In fact, it is commonly acknowledged that biodegradation, defined as the selective destruction of part of the molecules making up a petroleum crude by bacteria, can develop up to temperatures that can reach 70° C. to 80° C. Such temperatures are common in the deep marine domain which is one of the zones where oil prospecting is currently the most active. This biodegradation, whose effect is generally to weight the oil, to raise its viscosity and to decrease its API degree, is a major risk for oil companies whose deep-sea drilling operations involve considerable financial investments. Any method allowing this risk to be reduced is thus of major interest for these companies.

BACKGROUND OF THE INVENTION

The following documents, mentioned in the course of the description hereafter, illustrate the state of the art:

[1] Horstad I., Larter S. R., Mills N., *A quantitative model of biological petroleum degradation within the Brent group reservoir*, Org. Geochem., 19, pp. 107-117,

[2] Côme J. M., *Experimentation et modélisation de procédés in situ de dépollution par biodégradation aérobie des aquiferes contamines par des hydrocarbures*, thesis dissertation, pp. 75-93, april 95,

[3] Z. (Alan) Yu, G. Cole, G. Grubitz and F. Peel, *How to predict biodegradation risk and reservoir fluid quality*, WorldOil.com April 2002, Vol. 223 No. 4,

[4] B. A. Cragg, K. M. Law, G. M. O'Sullivan, R. J. Parkers, *Bacterial profiles in deep sediments of the Alboran sea, western Mediterranean site 976-978*, Proceedings of the Ocean Drilling Program, Scientific Results, Vol. 161, p. 433-438, 1999,

[5] Ian M. Head, D. Martin Jones and Steve R. Larter, *Biological activity in the deep subsurface and the origin of heavy oil*, Nature, Vol. 426 20, Nov. 2003,

[6] B. Carpentier and L. Martin: patent FR-2,830,646,

[7] Larter et al., *Biodegradation rates assessed geologically in a heavy oil field*, implications for the deep, slow (Largo) biosphere PHENIX, Goldschmidt, 2000,

[8] I. Kowalewski et al., *Geochemical study of biodegraded heavy oils of Wabasca sand deposits (Canada)*, Abstract, Vol. 1, p. 87, 20th International Meeting on Organic Geochemistry, Nancy, 10-14 Sep. 2001,

[9] J. P. Vandecasteele, *Microbiologie pétrolière: concepts, implications environnementales, applications industrielles*, Vol. 2, chapter 12, pp. 629-675, Collection Publications de l'Institut Frangais du Pétrole, Ed. Technip, 2005, Biodegradation of an oil consisting of organic matter in form of hydrocarbon-containing molecules is an alteration phenomenon caused by the oxidation of certain hydrocarbon-containing molecules by micro-organisms or bacterial flora. The bacteria consume these hydrocarbon-containing molecules as they breathe and thus get the elements that are essential for their growth and their replication. Biodegradation leads to the formation of a heavy oil that is difficult to produce and commercially less profitable. The study of this phenomenon arouses renewed interest with the development of deep-sea exploration where the presence of heavy oil is a major risk. There are currently few means available for predicting biodegradation risks, whereas the economic need for developing quantitative tools is increasingly great.

Biodegradation thus is a bio-geochemical process that has similarities to a cold combustion operated by micro-organisms. A bacterium capable of degrading hydrocarbon-containing compounds can in fact be considered to be a hydrocarbon-consuming machine using electron-accepting ions (that can be compared to an oxidizer) and rejecting a reducer.

A known model describing the biodegradation of a field from data relative to the Gullfaks field in the North Sea is described in the publication by Horstad et al. [1].

According to this model, filling of a trap with hydrocarbons at a constant flow rate is envisaged. Water saturated with electron acceptors also circulates with a constant flow rate. The field has a simple parallelepipedic symmetry. During filling in the transition zone, the destruction of four n-alkanes is calculated by means of conventional first-order kinetic laws obtained in the laboratory. The mass balance consists of a kinetic hydrocarbon destruction term and the terms of hydrocarbon and electron acceptor supply by convection. The degradation is double, by air breathing and by sulfato-reduction.

In this system, the electron acceptor supply is the limiting factor. The parameters controlling the system are the thickness of the transition zone and the flow rate of the water below the transition zone. The results obtained by means of this type of model appear to be hardly realistic. This is due to the selection of the balances and of the reaction kinetics, the latter being related to the lack of knowledge about the bacterial kinetics and the attack mechanisms developed by the bacteria.

Models integrating a more complex approach of the porous medium and of the material transport are commonly used to simulate biodegradation in shallow polluted layers, notably the SIMUSCOP model (IFP, France), developed on the basis of research work described in reference [2]; it allows to grid (to discretize into cells) in 3D a subsoil and to calculate the biodegradation by air breathing on the BTEX (Benzene, Toluene, Ethylbenzene, Xylene).

The BIO1D software developed by the ECHOSCAN Company (Canada) can also be mentioned, as well as RT3D or PARSSIM1 (Texas University). The documentation relative to these models is available at the following Internet addresses:

BIO1D Model:
http://people.becon.org/~echoscan/13-22.htm
PARSSIM Model:
http://www.ticam.utexas.edu/~shuyu/pssProject/
RT3D Model:
http://bioprocess.pnl.gov/rt3d.htm A bibliography concerning biodegradation simulation within the scope of depollution is also available at the following address:
http://www.nal.usda.gov/wqic/Bibliographies/qb9406.html In most of these models, only the hydrocarbon-containing molecules of high water solubility are taken into account (BTEX). Oil is present in dissolved form and moves only by diffusion. Sometimes, residual oil moving by convection is also considered. Although the oil saturations involved are not the same as in a petroleum reservoir and although the emphasis is put on the material transports in the aquifer, the problematics is applicable to reservoirs. Unfortunately, application of such models to the sphere of oil prospecting is nearly impossible because of the difference in the time scales (some days to several ten years for pollution problems in contrast with several thousand years for geologic events) and of the difficulty acquiring the input data of the models.

Another method proposed for the petroleum industry is the "BDI" developed by BHP Billiton Petroleum [3]. It is an empirical simplified approach with a limited number of parameters whose result is a biodegradation index that can be converted to API degree by means of a chart.

The relation used for calculating the BDI is as follows [3]:

$$BDI = \sum_{i=1}^{N} ((T_i - T_c) \times \Delta t_i)/C$$

where:

N is the number of stages selected, $T_i$ is the temperature of the reservoir, $T_c$ is the critical bacterial activity temperature (usually 65° C.), $\Delta t_i$ is the time in Ma since filling of the trap, C is an adjustment parameter depending on the basin.

The differences between the BDI method and the method according to the invention are as follows:

The BDI method is purely empirical and requires definition of an adjustment parameter that cannot be a priori determined. Furthermore, this method implies that biodegradation occurs throughout the residence time of the oil in the reservoir (from its filling till now).

Another method, which is the subject of patent FR-2,830,646 [6], allows to model the progressive biodegradation of hydrocarbons trapped in a petroleum reservoir or trap studied, by the action of a bacterial population in an aquifer. This method requires a large amount of input data: data relative to the reservoir studied, concerning the shape and the height of the reservoir, the physical characteristics of the porous medium, the thickness of the transition zone between the hydrocarbons and the water, the composition of the hydrocarbons, of the flow of electron acceptors entering the reservoir and data relative to the bacterial population in the aquifer. This approach is therefore difficult to apply in cases where few data are available.

SUMMARY OF THE INVENTION

The invention relates to a method of evaluating the biodegradation, through the action of bacteria, of hydrocarbons trapped in a geologic structure. This structure is first discretized into a set of cells so as to perform afterwards modelling of the basin in order to determine physical and geometrical characteristics relative to said structure. The method comprises the following stages:

evaluating the mass $M_{hp}$ of hydrocarbons present in said structure without taking account of the biodegradation, from said physical and geometrical characteristics, estimating the number of bacteria present in said structure and taking part in the biodegradation, estimating a hydrocarbon consumption of said bacteria, determining a hydrocarbon filling time for said structure, evaluating the mass $M_{hb}$ of hydrocarbons consumed by biodegradation, from the number of bacteria, their hydrocarbon consumption and the filling time, and evaluating the biodegradation from the mass ratio R of consumed hydrocarbons $M_{hb}$ to the mass of hydrocarbons $M_{hp}$.

The number of bacteria taking part in the biodegradation can be estimated by considering that the bacteria are located in a transition zone defined at the level of an interface, within the structure, between an aquifer and said hydrocarbons. In this case, the number of bacteria taking part in the biodegradation can be determined from a factor characterizing the volume ratio between said structure and said transition zone.

According to the invention, it is possible to take into account only the cells whose temperature is lower than a limit temperature at which there is no more biological activity, and/or the cells whose hydrocarbon saturation is higher than a given saturation threshold (of the order of 80% for example).

Finally, according to the invention, a correspondence can be established between the biodegradation degree corresponding to Peter and Moldowan's scale and mass ratio R, using for example the correspondence table as follows:

| | R × 100 | | | | | |
|---|---|---|---|---|---|---|
| | 0-10 | 11-50 | 51-60 | 61-75 | 76-90 | >91 |
| Biodegradation degree | 1 | 2 | 3 | 4 | 5 | 6 |

BRIEF DESCRIPTION OF THE FIGURES

Other features and advantages of the method according to the invention will be clear from reading the description hereafter of embodiments given by way of non limitative example, with reference to the accompanying figures wherein.

DETAILED DESCRIPTION

The method according to the invention allows to evaluate the biodegradation of hydrocarbons trapped in a geologic structure such as a petroleum reservoir, i.e. to evaluate the amount of molecules making up these hydrocarbons destroyed during filling of the structure (referred to as trap). The molecules are destroyed through the action of a bacterial population located in an aquifer that is below and in contact with the hydrocarbons. This evaluation allows for example to determine the development conditions of a petroleum reservoir.

The basic idea consists in calculating the mass ratio of oil disappeared through biodegradation to the initial oil. This method is generally implemented in parallel with or after basin modelling. It mainly comprises three stages:

1—Estimating the amount of hydrocarbons present in a trap without taking account of the biodegradation, 2—Calculating the amount of hydrocarbons consumed through biodegradation, 3—Evaluating the biodegradation of the trapped hydrocarbons from these two amounts.

1—Estimation of the Amount of Trapped Hydrocarbons without Taking Account of the Biodegradation The amount of hydrocarbons trapped in a petroleum reservoir or in any other trap, without taking account of the biodegradation, can be estimated for example by means of the mass of trapped hydrocarbons denoted by $M_{hp}$. This amount can be estimated from the following formula:

$$M_{hp}=S_m \times V_p \times \phi_m \times 1000 \times \rho_h$$

with:

$S_m$: the mean hydrocarbon saturation of the reservoir (in fraction)

$\phi_m$: the mean porosity of the reservoir (in fraction)

$\rho_h$: the hydrocarbon density (in g/cm$^3$)

$V_p$: the volume of the trap (in cm$^3$).

The mass of trapped hydrocarbons $M_{hp}$ is then estimated in mg.

The mass of trapped hydrocarbons $M_{hp}$ thus represents the mass of hydrocarbons trapped during filling of the trap, assuming that no biodegradation took place.

Figure 1:
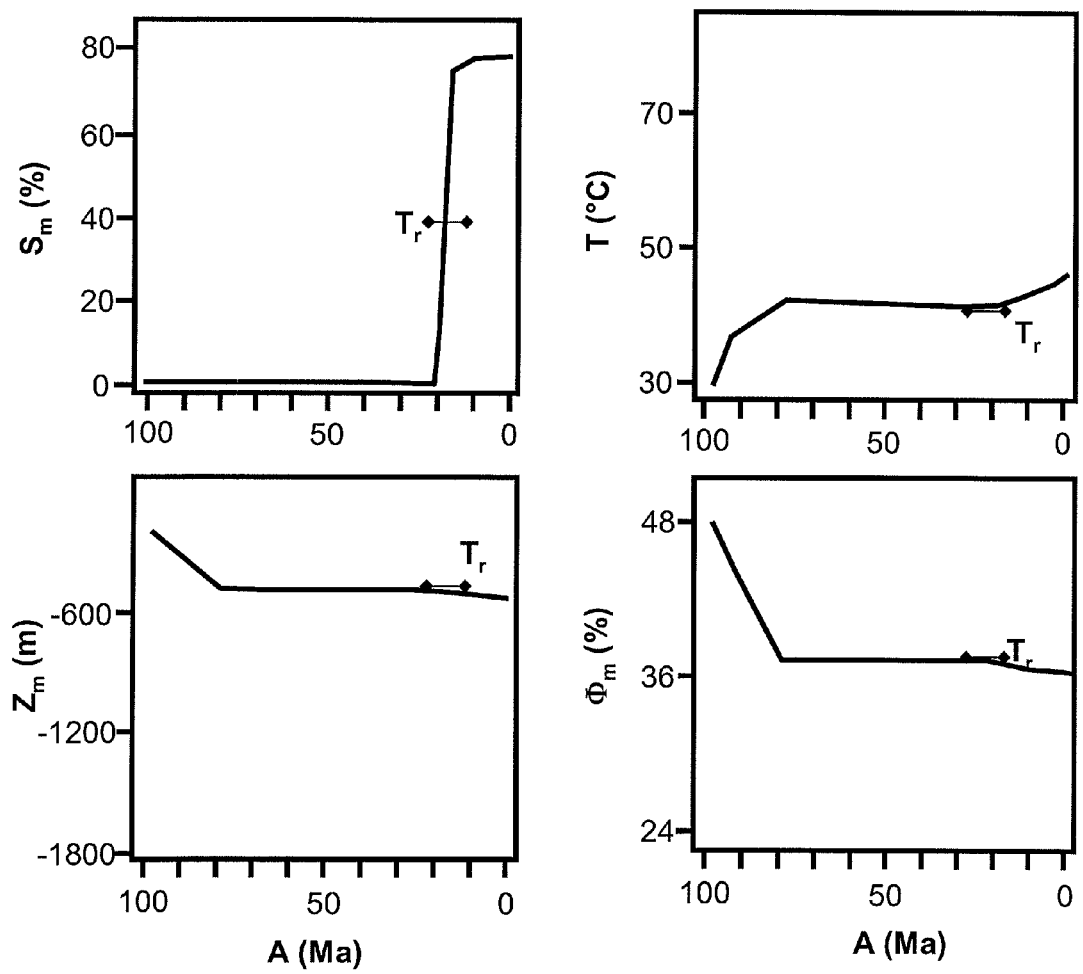
FIG. 1 shows the result of a basin modelling; it shows, during the geologic time in abscissa, the evolution of the oil saturation, of the depth, of the temperature and of the porosity of a cell where the percentage of biodegraded oil as a function of time is sought.

According to an embodiment of the invention, the mean saturation $S_m$, the mean porosity $\phi_m$, and the oil density $\rho_h$, can be determined, automatically or manually, from the results calculated by a numerical basin model such as TEMIS (IFP, France), well known to the man skilled in the art. A basin model is a discretized representation of a geologic basin in a multitude of cells forming a grid. The simulator of a basin model allows to calculate, in each cell, a large number of parameters such as: the mean saturation, the mean porosity, the oil density, the filling time, temperature and depth, etc. FIG. 1 illustrates results obtained from a basin modelling and it shows the evolution of the oil saturation ($S_m$), of the depth ($Z_m$), the temperature (T) and the mean porosity ($\phi_m$) of a given cell where the percentage of biodegraded oil as a function of time is sought. In this example, saturation ($S_m$) at the end of the filling time is 80%, the filling time ($T_r$) was 4 million years, the depth of the trap ($Z_m$) during filling was 500 m, its temperature (T) was 40° C. and its porosity ($\phi_m$) was 37%.

According to other embodiments, mean saturation $S_m$, mean porosity $\phi_m$ and oil density $\rho_h$ can be determined from prior surveys, laboratory analyses of samples taken for example from other traps already drilled in the same basin, . . . .

If no measurement relative to the oil density $\rho_h$ is available, this value is usually considered to be 0.8 g/cm$^3$.

2—Evaluation of the Amount of Hydrocarbons Consumed by Biodegradation

Figure 2:
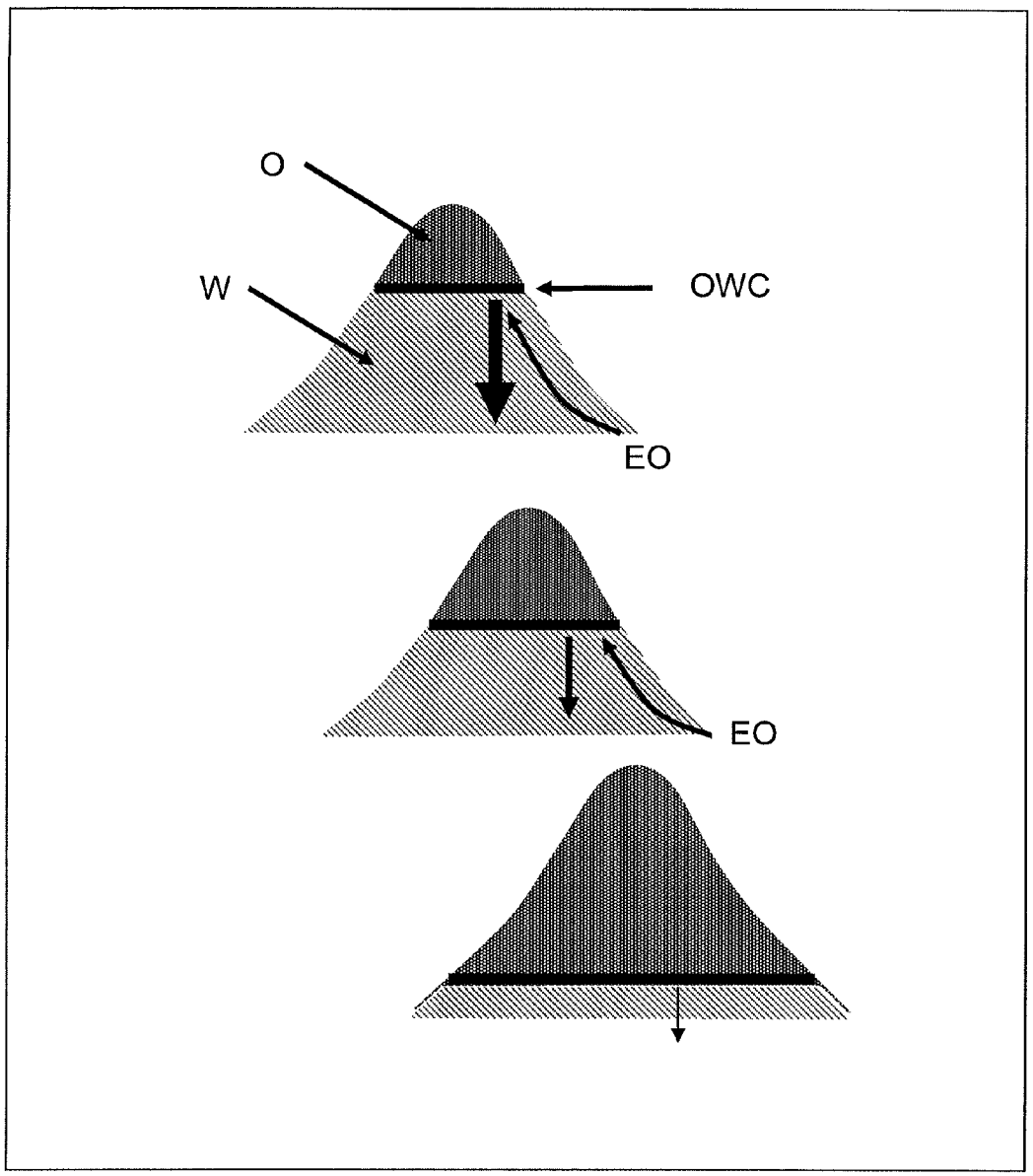
FIG. 2 shows a geologic trap during filling with the displacement of a water/hydrocarbon transition zone.

Determination of the Biodegradation Conditions:

According to the invention, three hypotheses characterize the biodegradation:

the biodegradation occurs during the trap filling period, the biodegradation occurs on contact (OWC) between the water (W) and the oil (O), as illustrated by FIG. 2, which also shows filling of the geologic trap as the non-biodegraded oil (EO) flows in, the biodegradation occurs only if the temperature within the trap is lower than a fixed threshold set by a user, this threshold value being usually taken equal to 80° C.

Thus, according to the method, it is necessary to characterize the interface (OWC) between the water and the oil, to determine on the one hand the trap filling period ($T_r$) and, on the other hand, the maximum temperature ($T_{max}$) within the trap.

To take account of the fact that the biodegradation occurs only at the level of the interface between the oil and the water (referred to as "transition zone"), and not over the entire column of oil, the method involves evaluating the volume ratio (E) between the trap and the transition zone. The ratio of the height of the transition zone to the height of the column of oil contained in the trap can be used for example. This ratio can be evaluated from the surveys carried out by S. Larter et al. [7], which show that usually only 2% of the reservoir height is used by the biodegradation. A constant value of the order of 0.02 can thus be proposed for ratio E.

The filling time ($T_r$) is determined from the determination of the ages of filling start $T_d$ and of filling end $T_f$:

$$T_r=T_d-T_f$$

We consider that the filling start within a cell is characterized by an oil saturation that is above 10% and increasing. We consider that the filling end within the cell is characterized by an oil saturation that reaches 80% and is more or less constant (but always above 70%).

According to an embodiment of the invention, like the mean saturation $S_m$ and the mean porosity $\phi_m$, the ages of filling start $T_d$ and of filling end $T_f$ can be determined automatically or manually, from the graphic and/or numerical results calculated by means of a numerical basin model.

For the limit temperature at which there is no more biological activity ($T_{max}$), it is generally accepted that 70° C.-80° C. is the maximum range of temperatures for a bacterial activity that is sufficient to generate biodegradation of the oils in a geologic medium [7].

Determination of Data Relative to the Bacterial Population

Once the biodegradation conditions determined, it is necessary to evaluate the number of bacteria ($N_{bact}$) per unit of volume taking part in the biodegradation during filling, as well as the hydrocarbon consumption by a bacterium and per unit of time ($HC_{bact}$).

According to an embodiment, we can estimate that the number of bacteria ($N_{bact}$) decreases exponentially with depth, and use for each cell of the basin model the following formula proposed by Cragg et al. [4]:

$$N_{bact}=10^{(7.95-(0.64 \times log(Z_m)))}$$

with:

$Z_m$: mean depth of a given cell during time $T_r$.

According to an embodiment of the invention, like the mean saturation $S_m$ and the mean porosity $\phi_m$, the mean depth can be determined automatically or manually from graphic and/or numerical results calculated by means of a numerical basin model.

However, to take account of the fact that biodegradation takes place only at the level of the interface between the oil and the water, and not over the entire column of oil, the method estimates more precisely the number of bacteria per unit of volume taking part in the biodegradation during filling, i.e. at the level of the water/oil transition zone.

According to an embodiment, $N_{bact}$ is converted by means of a scale factor (E) characterizing the volume ratio between the trap and the transition zone. Thus, the number of bacteria per unit of volume taking really part in the biodegradation can be written as follows:

$$E \times N_{bact}=E \times 10^{(7.95-(0.64 \times log(Z_m)))}$$

According to other embodiments, the number of bacteria per unit of volume at the level of the transition zone can be determined from the temperature at the time of filling, because the temperature is related, via the thermal gradient, to the depth of burial.

The hydrocarbon consumption ($HC_{bact}$) by a bacterium and per unit of time is constant on the geologic scale. According to an embodiment, it is possible to determine a mean value for $HC_{bact}$ from an estimation of the mean carbon consumption of a bacterium ($C_{bact}$).

According to Larter et al. [7], the mean carbon consumption of a bacterium ($C_{bact}$) usually ranges between $10^{-11}$ and $10^{-14}$ µg C per second. Furthermore, the ratio of the mass of carbon (C) consumed to the mass of hydrocarbons (HC) consumed ($R_{ch}$) is of the order of 0.8 gC/gHC. Thus:

$$HC_{bact} = \frac{C_{bact}}{R_{ch}}$$

$HC_{bact}$ can also be determined from prior surveys, from laboratory analyses of samples taken from traps already drilled, notably from the evaluation of mass balances performed on biodegraded reservoirs already discovered.

The mass of hydrocarbon consumed by biodegradation ($M_{hb}$) can then be written as follows:

$$M_{hb} = \frac{N_{bact} \times E \times V_p \times C_{bact} \times T_r}{R_{ch}}$$

with:
$N_{bact}$: number of bacteria per unit of volume (1/cm³)
E: scale factor (without unit)
$V_p$: volume of the trap (cm³)
$C_{bact}$: mean carbon consumption per unit of time (mg/year)
$T_r$: filling time (year)
$R_{ch}$: ratio of the mass of carbon consumed to the mass of hydrocarbon consumed (mg C/mg HC)
$M_{hb}$: mass of hydrocarbon consumed by biodegradation (mg)

3—Evaluation of the Biodegradation of the Trapped Hydrocarbons

According to the method, an evaluation of the biodegradation of the trapped hydrocarbons is given by ratio R defined as follows:

$$R = \frac{\text{mass of oil consumed by biodegradation}}{\text{mass of oil present without biodegradation}} = \frac{M_{hb}}{M_{hp}}$$

We can thus write:

$$R = \frac{M_{hb}}{M_{hp}} = \frac{N_{bact} \times E \times V_p \times C_{bact} \times T_r}{S_m \times V_p \times \phi_m \times 1000 \times \rho_h \times R_{ch}} = \frac{N_{bact} \times E \times C_{bact} \times T_r}{S_m \times \phi_m \times 1000 \times \rho_h \times R_{ch}}$$

The evaluation method takes account of the biodegradation conditions. Ratio R can thus be determined:

$$R = \frac{N_{bact} \times E \times C_{bact} \times T_r}{S_m \times \phi_m \times \rho_h \times 1000 \times R_{ch}} = \frac{N_{bact} \times E \times HC_{bact} \times T_r}{S_m \times \phi_m \times \rho_h \times 1000}$$

Other Embodiments

According to an embodiment, calculation of this ratio R can be carried out only on cells with a high current hydrocarbon saturation. These cells can be selected automatically by basin modelling or manually, by means of criteria based on the high oil saturation of the cells of the basin model. Cells whose mean oil saturation is above 80% can for example be selected.

According to an embodiment, calculation of this ratio R can be carried out only on cells whose temperature is lower than the limit temperature at which there is no more biological activity $T_{max}$.

Finally, according to an embodiment, this ratio R can be converted to "biodegradation degree" such as the degrees proposed by Moldowan's scale [5] via relations based on heavy metal contents (I. Kowalewski et al., 2001, [8], and J. P. Vandecasteele, 2005, [9]) and/or the disappeared n-alkanes % [5].

Calculation of the biodegradation degree is then carried out by means of the following correspondence table:

|  | R × 100 | | | | | |
|---|---|---|---|---|---|---|
|  | 0-10 | 11-50 | 51-60 | 61-75 | 76-90 | >91 |
| Biodegradation degree | 1 | 2 | 3 | 4 | 5 | 6 |

For example, for a ratio R equal to 0.3, the biodegradation degree is 2.

The invention thus relates to a method of quantifying the relative percentage of biodegraded oil in relation to the total trapped oil, i.e. the oil that would be present in the reservoir if there had been no biodegradation. This quantification can then allow evaluation, according to the conventional Peter and Moldowan scale [5], of the biodegradation degrees of the oil in place.

The method according to the invention is based on biology work [4-7] and it implies that biodegradation occurs at the OWC during the trap filling time and not during the residence time of the oil (preservation time) in the trap.

Figure 3:
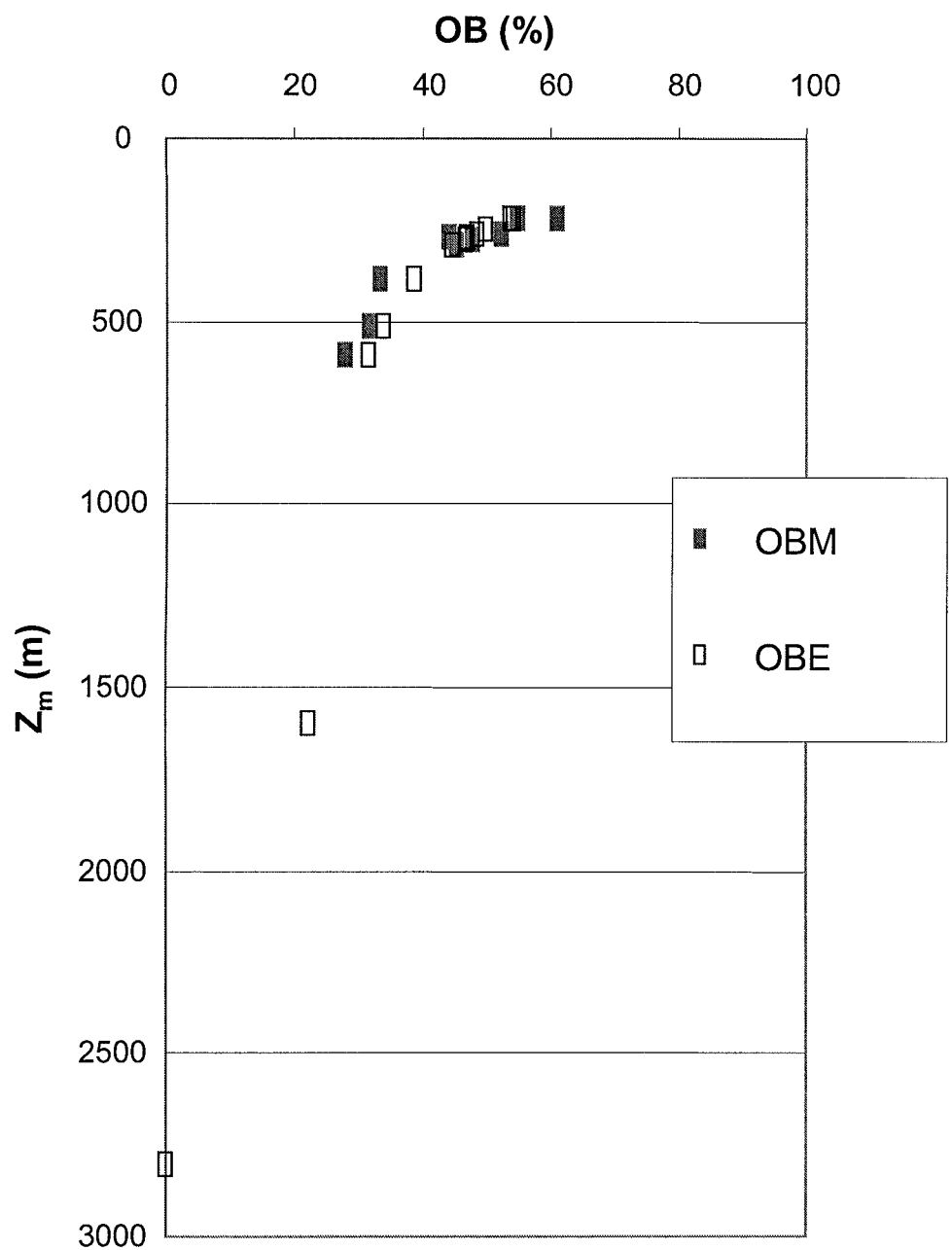
FIG. 3 shows an example of comparison between the biodegraded oil percentages determined by means of the method according to the invention and determined by measurements performed on oil samples from the basin.

An example of validation of the method according to the invention is shown in FIG. 3 for a case studied in Brazil. The comparison between the percentages of oil disappeared by biodegradation (OB) obtained from measurements performed on production oil samples (OBM) and those evaluated from the invention (OBE) shows the good prediction capacity of the invention.

By taking account of the geologic reservoir filling time and of the depth at which this filling occurs, the method allows to carry out much more realistic estimations of the biodegradation degree of the oil in place than with prior methods. It thus allows to better select the reservoir development conditions and to better evaluate the operating costs.

The invention claimed is:
1. A computer-implemented method of evaluating the amount of biodegradation, through the action of bacteria, of hydrocarbons trapped in a basin discretized into a set of cells, comprising:
estimating a mean hydrocarbon saturation of the basin ($S_m$), a mean porosity of the basin ($\Phi_m$), and a hydrocarbon density ($\rho_h$);
calculating, in a computer processor, a mass $M_{hp}$ of hydrocarbons present in the basin, without taking account of the biodegradation, as a product comprising the mean hydrocarbon saturation of the basin ($S_m$), the mean porosity of the basin ($\Phi_m$), the hydrocarbon density ($\rho_h$), and a volume ($V_p$) wherein hydrocarbons are trapped;

executing, in the computer processor, a computer-implemented basin simulation, in order to determine physical and geometrical characteristics of the basin, the physical and geometrical characteristics comprising at least a hydrocarbon filling time ($T_r$) for the basin, and a mean depth ($Z_m$) of a given cell in the basin during the filling time;

estimating the number of bacteria ($N_{bact}$) present in the basin and taking part in the biodegradation, including executing, in the computer processor, the formula $N_{bact}=10^{(7.95-(0.64*log(Zm)))}$;

estimating a hydrocarbon consumption of the bacteria, from a ratio of an estimation of a mean carbon consumption of a bacterium ($C_{bact}$) and a ratio ($R_{ch}$) of a mass of carbon consumed to a mass of hydrocarbons consumed, wherein $C_{bact}$ ranges between $10^{-11}$ and $10^{-14}$ µg C per second, and $R_{ch}$ is in the order of 0.8 gC/gHC;

calculating, in the computer processor, a mass $M_{hb}$ of hydrocarbons consumed by biodegradation, as a product comprising the number of bacteria ($N_{bact}$), the hydrocarbon consumption of a bacterium ($C_{bact}$), the hydrocarbon filling time for the basin ($T_r$), the volume ($V_p$) wherein hydrocarbons are trapped, and the inverse of the ratio of the mass of carbon consumed to the mass of hydrocarbon consumed ($R_{ch}$);

evaluating and outputting the amount of biodegradation by calculating a mass ratio (R) of the mass of consumed hydrocarbons ($M_{hb}$) to the mass of hydrocarbons ($M_{hp}$).

2. A computer-implemented method as claimed in claim 1, wherein the number of bacteria taking part in the biodegradation is estimated by considering that the bacteria are located at the level of a transition zone defined at an interface, within the basin, between an aquifer and the hydrocarbons.

3. A computer-implemented method as claimed in claim 2, wherein the number of bacteria taking part in the biodegradation is determined from a factor characterizing the volume ratio between the basin and the transition zone.

4. A computer-implemented method as claimed in claim 1, further comprising:

executing, in the computer processor, the computer-implemented basin simulation, in order to determine a temperature in each cell, and only taking into account, for purposes of the mass ratio (R) calculation, the cells whose temperature is lower than a limit temperature at which there is no more biological activity.

5. A computer-implemented method as claimed in claim 1, further comprising:

executing, in the computer processor, the computer-implemented basin simulation, in order to determine a hydrocarbon saturation in each cell, and only taking into account, for purposes of the mass ratio (R) calculation, the cells whose hydrocarbon saturation is higher than a given saturation threshold.

6. A computer-implemented method as claimed in claim 5, wherein the saturation threshold is of the order of 80%.

7. A computer-implemented method as claimed in claim 1, wherein a correspondence is established between the biodegradation degree corresponding to Peter and Moldowan's scale and mass ratio R, including the following correspondence table:

| | R × 100 | | | | | |
|---|---|---|---|---|---|---|
| | 0-10 | 11-50 | 51-60 | 61-75 | 76-90 | >91 |
| Biodegradation degree. | 1 | 2 | 3 | 4 | 5 | 6 |

8. A computer-implemented method, including a simulation of basins, for determining and outputting the amount of biodegradation, caused by the action of bacteria, of hydrocarbons trapped in a basin discretized into a set of cells, comprising:

obtaining values for a mean hydrocarbon saturation of the basin ($S_m$), a mean porosity of the basin ($\Phi_m$), and a hydrocarbon density ($\rho_h$);

determining, in a computer processor, a mass $M_{hp}$ of hydrocarbons present in the basin, without taking account of the biodegradation, as a product comprising the mean hydrocarbon saturation of the basin ($S_m$), the mean porosity of the basin ($\Phi_m$), the hydrocarbon density ($\rho_h$), a volume ($V_p$) wherein hydrocarbons are trapped;

executing, in the computer processor, a computer-implemented basin simulation, in order to determine physical and geometrical characteristics of the basin, the physical and geometrical characteristics comprising at least a hydrocarbon filling time ($T_r$) for the basin, and a mean depth ($Z_m$) of a given cell in the basin during the filling time;

determining, in the computer processor, a number of bacteria ($N_{bact}$) present in the basin and taking part in the biodegradation, including executing, in the computer processor, the formula $N_{bact}=10^{(7.95-(0.64*log(Zm)))}$;

determining, in the computer processor, a hydrocarbon consumption of the bacteria, from a ratio of an estimation of a mean carbon consumption of a bacterium ($C_{bact}$) and a ratio ($R_{ch}$) of a mass of carbon consumed to a mass of hydrocarbons consumed, wherein $C_{bact}$ ranges between $10^{-11}$ and $10^{-14}$ µg C per second, and $R_{ch}$ is in the order of 0.8 gC/gHC;

determining, in the computer processor, a mass $M_{hb}$ of hydrocarbons consumed by biodegradation, as a product comprising the number of bacteria ($N_{bact}$), the hydrocarbon consumption of a bacterium ($C_{bact}$), the hydrocarbon filling time for the basin ($T_r$), the volume ($V_p$) wherein hydrocarbons are trapped, and the inverse of the ratio of the mass of carbon consumed to the mass of hydrocarbon consumed ($R_{ch}$);

determining, in the computer processor, and outputting the amount of biodegradation by calculating a mass ratio (R) of the mass of consumed hydrocarbons ($M_{hb}$) to the mass of hydrocarbons ($M_{hp}$).

9. A computer-implemented method as claimed in claim 8, wherein the number of bacteria taking part in the biodegradation is determined by considering that the bacteria are located at the level of a transition zone defined at an interface, within the basin, between an aquifer and the hydrocarbons.

10. A computer-implemented method as claimed in claim 9, wherein the number of bacteria taking part in the biodegradation is determined from a factor characterizing the volume ratio between the basin and the transition zone.

11. A computer-implemented method as claimed in claim 8, further comprising:

executing, in the computer processor, the computer-implemented basin simulation, in order to determine a temperature for each cell, and only taking into account, for purposes of the mass ratio (R) calculation, the cells whose temperature is lower than a limit temperature at which there is no more biological activity.

12. A computer-implemented method as claimed in claim 8, further comprising:
executing, in the computer processor, the computer-implemented basin simulation, in order to determine a hydrocarbon saturation for each cell, and only taking into account, for purposes of the mass ratio (R) calculation, the cells whose hydrocarbon saturation is higher than a given saturation threshold.

13. A computer-implemented method as claimed in claim 12, wherein the saturation threshold is of the order of 80%.

14. A computer-implemented method as claimed in claim 8, wherein a correspondence is established between the biodegradation degree corresponding to Peter and Moldowan's scale and mass ratio R, including the following correspondence table:

|  | R × 100 | | | | | |
| --- | --- | --- | --- | --- | --- | --- |
|  | 0-10 | 11-5- | 51-60 | 61-75 | 76-90 | >91 |
| Biodegradation degree | 1 | 2 | 3 | 4 | 5 | 6. |

15. A computer-implemented method, including a simulation of basins, for determining and outputting the amount of biodegradation, caused by the action of bacteria, of hydrocarbons trapped in a basin, comprising:
obtaining values from at least one of physical sample data, simulation results, or default values, for a mean hydrocarbon saturation of the basin ($S_m$), a mean porosity of the basin ($\Phi_m$), and a hydrocarbon density ($\rho_h$);
determining, in a computer processor, a mass $M_{hp}$ of hydrocarbons present in the basin, without taking account of the biodegradation, as a product of the mean hydrocarbon saturation of the basin ($S_m$), the mean porosity of the basin ($\Phi_m$), the hydrocarbon density ($\rho_h$), the volume ($V_p$) wherein hydrocarbons are trapped, and a first constant factor;
executing, in the computer processor, a computer-implemented basin simulation, in order to discretize the basin into a set of cells;
executing, in the computer processor, the computer-implemented basin simulation, in order to determine physical and geometrical characteristics of the basin, comprising at least a hydrocarbon filling time ($T_r$) for the basin, and a mean depth ($Z_m$) of a given cell in the basin during the filling time;
determining, in the computer processor, a number of bacteria ($N_{bact}$) present in the basin and taking part in the biodegradation, including executing, in the computer processor, the formula $N_{bact}=10^{(7.95-(0.64*log(Zm)))}$;
determining, in the computer processor, a hydrocarbon consumption of the bacteria, from a ratio of an estimation of a mean carbon consumption of a bacterium ($C_{bact}$) and a ratio ($R_{ch}$) of a mass of carbon consumed to a mass of hydrocarbons consumed, wherein $C_{bact}$ ranges between $10^{-11}$ and $10^{-14}$ μg C per second, and $R_{ch}$ is in the order of 0.8 gC/gHC;
determining, in the computer processor, a mass $M_{hb}$ of hydrocarbons consumed by biodegradation, as a product of the number of bacteria ($N_{bact}$), the hydrocarbon consumption of a bacterium ($C_{bact}$), the hydrocarbon filling time for the basin ($T_r$), the volume ($V_p$) wherein hydrocarbons are trapped, and a second constant factor, wherein the product is divided by the ratio of the mass of carbon consumed to the mass of hydrocarbon consumed ($R_{ch}$);
determining, in the computer processor, and outputting the amount of biodegradation by calculating a mass ratio (R) of the mass of consumed hydrocarbons ($M_{hb}$) to the mass of hydrocarbons ($M_{hp}$).

* * * * *